(12) United States Patent
Tsai

(10) Patent No.: US 9,494,571 B2
(45) Date of Patent: Nov. 15, 2016

(54) METHODS OF TESTING FOR INTRACELLULAR PATHOGENS

(75) Inventor: Theodore Tsai, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/583,619

(22) PCT Filed: Mar. 7, 2011

(86) PCT No.: PCT/IB2011/001057
§ 371 (c)(1),
(2), (4) Date: Sep. 7, 2012

(87) PCT Pub. No.: WO2011/110955
PCT Pub. Date: Sep. 15, 2011

(65) Prior Publication Data
US 2013/0004942 A1    Jan. 3, 2013

Related U.S. Application Data

(60) Provisional application No. 61/339,764, filed on Mar. 8, 2010.

(51) Int. Cl.
*G01N 33/50*  (2006.01)
(52) U.S. Cl.
CPC .................................. *G01N 33/5008* (2013.01)
(58) Field of Classification Search
None
See application file for complete search history.

(56) References Cited

U.S. PATENT DOCUMENTS

2003/0203868 A1  10/2003 Bushman et al.
2010/0331211 A1  12/2010 Mosticone et al.

FOREIGN PATENT DOCUMENTS

FR       2928655 A1    9/2009
WO   WO-2006062596    6/2006

OTHER PUBLICATIONS

Johnson TC, McLaren LC. J Bacteriol. Sep. 1965;90(3):565-70.*
Forrer C.B. et al. Comparison of Vancomycin and Penicillin for Viral Isolation. Journal of Clinical Microbiology, Aug. 1982, p. 295-298 vol. 16, No. 2.*
Reyes M et al. Respiratory infection and iatrogenic diarrhea in Honduras and El Salvador during the 1991-1992 season. Am J Trop Med Hyg. Mar. 1996;54(3):260-4.*
Ge Q et al. RNA interference of influenza virus production by directly targeting mRNA for degradation and indirectly inhibiting all viral RNA transcription. Proc Natl Acad Sci U S A. Mar. 4, 2003;100(5):2718-23. Epub Feb. 19, 2003.*
Takaya Yamanaka et al. Isolation of Influenza A and B Viruses in HeLa Cells. Microbiol. Immunol., 39(5), 361-363, 1995.*
Fan et al. A modified single-tube one-step product-enhanced reverse transcriptase (mSTOS-PERT) assay with heparin as DNA polymerase inhibitor for specific detection of RTase activity. Journal of Clinical Virology 37 (2006) 305-312.*
Kistner et al. Development of a mammalian cell (Vero) derived candidate influenza virus vaccine. Vaccine. May-Jun. 1998;16(9-10):960-8.*
P.R. Krause (Emerging Infectious Diseases, vol. 7, No. 03 Supplement, Jun. 2001).*
O.-W. Merten (Cytotechnology 39: 91-116, 2002).*
Matrosovich et al. New low-viscosity overlay medium for viral plaque assays. Virology Journal 2006, 3:63.*
Bitko et al. (2005). "Inhibition of respiratory viruses by nasally administered siRNA," Nat Med. 11(1):50-55.
Qing et al. (2003). "RNA interference of influenza virus production by directly targeting mRNA for degradation and indirectly inhibiting all viral RNA transcription," 100(5):2718-2723.
International Search Report mailed on Sep. 30, 2011, for International Patent Application No. PCT/IB2011/001057, filed on Mar. 7, 2011.
Cutrone et al. (2005). "Some Oral Poliovirus Vaccines Were Contaminated with Infectious SV40 after 1961," Amer Assc Cancer Res 22(65):10273-10279.
European Pharmacopeia (2008). "Avian viral vaccines: tests for extraneous agents in seed lots," European Pharmacopeia, vol. 6, No. 2.6.24, p. 198-201.
European Pharmacopoeia (2008). "Tests for extraneous agents in viral vaccines for Human Use" European Pharmacopoeia, vol. 6, No. 2.6.16, p. 190-191.
Guidance for Industry (2010). "Characterization and Qualification of Cell Substrates and Other Biological Materials Used in the Production of Viral Vaccines for Infectious Disease Indications," U.S. Department of Health and Human Services, Food and Drug Administration, Center for Biologics Evaluation and Research, 50 pages.
Harrison et al. (1971). "Production and Evaluation of Formalin-Killed Chikungunya Vaccine" J Immunol 107(3):643-64 7.
Kenyon et al. (1975). "Preparation of Rocky Mountain Spotted Fever vaccine suitable for human immunization," J Clin Microbio. 1(6):500-503.
Kohanski et al. (2010). "How antibodies kill bacteria: from targets to networks," Nature Rev. 8:423-435.
Marchandin (2007). "MB7: Bacteriologie" in B2—Physiologie Bacterienne, Faculte de Medecine de Montpellier—Nimes, 5 pages.

(Continued)

*Primary Examiner* — Nick Zou
(74) *Attorney, Agent, or Firm* — Morrison & Foerster LLP

(57) ABSTRACT

A first intracellular pathogen in a biological sample that may contain more than one intracellular pathogen is studied by a method comprising the steps of (i) contacting the sample with a population of cells in the presence of an agent inhibiting the reproduction of a second intracellular pathogen; (ii) incubating the cells under conditions that permit the reproduction of the first intracellular pathogen; and (iii) testing material arising from step (ii) for the first intracellular pathogen.

26 Claims, No Drawings

(56) References Cited

OTHER PUBLICATIONS

Notice of Opposition filed on Jul. 28, 2015 against EP 2545172, 26 pages.
Oshel, D.D. (1962). "Federal Requirements and Procedures Used for Evaluation of Infectious Bronchitis Vaccines" Oxford Journal, pp. 173-178.
Public Health Agency of Canada (2010). "*Mycoplasma* Spp.: Pathogen Safety Data Sheet—Infectious Substances," online at http://www.phac-aspc.gc.ca/lab-bio/res/psds-ftss/mycoplasma-spp-eng.php, 4 pages.
U.S. Appl. No. 61/339,764, filed Mar. 8, 2010, to Theodore Tsai.
WHO Expert Committee on Biological Standardization, Fortieth Report, World Health Organization, Geneva, 1990, 86 pages.
Response to Notice of Opposition by Novartis AG for EP2545172, dated Jan. 13, 2016, 38 pages.
Assignment from Theodore Tsai to Novartis Vaccines and Diagnostics Inc. for U.S. Appl. No. 61/339,764, dated Dec. 17, 2010. 6 pages.
Assignment from Novartis Vaccines and Diagnostics Inc to Novartis AG, for U.S. Appl. No. 61/339,764, dated Dec. 21, 2010. 6 pages.

* cited by examiner

METHODS OF TESTING FOR INTRACELLULAR PATHOGENS

CROSS REFERENCE TO RELATED APPLICATIONS

This application is a U.S. National Phase patent application of PCT/IB2011/001057, filed Mar. 7, 2011, which claims priority to U.S. provisional patent application Ser. No. 61/339,764, filed Mar. 8, 2010, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002125900SeqListing.txt, date recorded: Aug. 30, 2012, size: 2 KB).

TECHNICAL FIELD

This invention relates to methods for studying intracellular pathogens in biological samples. More particularly, the invention relates to methods of studying biological samples containing more than one intracellular pathogen, and methods of observing or testing for the presence of a first intracellular pathogen in the presence of a second intracellular pathogen.

BACKGROUND ART

It may be of interest to study two different intracellular pathogens in the same biological sample, for example a sample isolated from a patient or from a cell culture, or to observe one intracellular pathogen in the presence of other intracellular pathogens. However, often the presence of one such pathogen interferes with observations of other pathogens.

For example, when the effects of intracellular pathogens are studied in assays leading to general phenotypic results ("phenotypic assays"), the observables are not necessarily specific for a particular pathogen. For example in virology, a plaque observed in a cell culture cannot necessarily be attributed to a given virus if a further pathogen capable of causing such plaques is also present.

However, it is often desirable to employ general phenotypic assays. Other, more specific methods of observing pathogens suffer from different drawbacks. Often, more specific methods are not as straightforward or rapid to perform. Such other methods may also require specific reagents which impose further limitations.

Immunological assays, for example, require antibodies to be available. The utility of immunological approaches may further be limited when antibodies are cross-reactive for multiple pathogens that may be present in the sample. For some diagnostic purposes, broad cross-reactivity of antibodies to related pathogens may be desirable. On the other hand, such cross-reactivity may make it impossible to study related and co-existing pathogens independently by immunological methods.

PCR-based testing for pathogens can be more specific. However, PCR-based methods require genomic sequences to be known for each pathogen of interest. Primers must be designed and optimized for each pathogen of interest.

The requirement for specific antibodies or primers limits the flexibility of both immunological and PCR-based methods, and in particular their utility for observing pathogens when the nature of the pathogen is not known. The utility of these specific methods may moreover be limited in the case of rapidly evolving pathogens, e.g., certain viruses, because mutations may occur in epitopes recognized by antibodies or in the sequences recognized by PCR primers.

It is an object of the invention to provide further and improved methods for studying intracellular pathogens of interest in a biological sample independently of other intracellular pathogens.

DISCLOSURE OF THE INVENTION

The invention provides a process for testing for a first intracellular pathogen in a biological sample, comprising the steps of:
  (i) contacting the sample with a population of cells in the presence of an inhibitory agent, wherein said agent inhibits the reproduction of a second intracellular pathogen;
  (ii) incubating the cells under conditions that permit the reproduction of said first intracellular pathogen; and
  (iii) testing material arising from step (ii) for said first intracellular pathogen.

According to the methods of the invention, biological samples can be tested rapidly. The invention allows biological samples to be tested for intracellular pathogens in a simple, straightforward manner, e.g., by a general phenotypic assay. Preferred methods allow an intracellular pathogen of interest to be studied independently of the (actual or suspected) presence in the sample of a further intracellular pathogen that would lead to the same, equivalent or similar result in such assays.

The invention also allows biological samples to be tested for intracellular pathogens in circumstances
  wherein the presence in the sample of one or more intracellular pathogens (e.g., the first intracellular pathogen of the methods defined above and in the claims) is unknown, and/or
  wherein the genomic sequences of one or more intracellular pathogens in the sample (e.g., the first intracellular pathogen of the methods defined above and in the claims) are unknown, and/or
  wherein antibodies to one or more intracellular pathogens in the sample (e.g., the first or the second intracellular pathogens of the methods defined above and in the claims) are unavailable, and/or
  an antibody to the second intracellular pathogen is not employed,
  wherein antibodies to two or more intracellular pathogens in the sample are cross reactive, and/or
  it is desirable to obtain test results rapidly.

The processes of the invention encompass embodiments wherein a test result of step (iii) is obtained within 12 months, or, e.g., within 9 months, 8 months, 7 months, 6 months, 5 months, 4 months, 3 months, 2 months, 1 month, 4 weeks, 3 weeks, 2 weeks, 1 week, 6 days, 5 days, 4 days, 3 days, 2 days, 1 day, or sooner.

Intracellular Pathogens of the Methods of the Invention

The first and second intracellular pathogens of the methods of the invention may encompass one or more intracellular pathogen selected from a prokaryote (i.e., a bacterium/bacteria), a eukaryote (including a protozoon/protozoa or a fungus/fungi), and/or a virus/viruses. The first intracellular pathogen is different from the second intracellular pathogen. The first and second pathogens may differ in any aspect that allows them to be differentially inhibited. For example, they may differ in order, family, genus, species, sub-species and/or strain.

The first intracellular pathogen may be a prokaryote, a eukaryote and/or a virus. Preferably, the first intracellular pathogen is a virus.

The second intracellular pathogen may be a prokaryote, a eukaryote and/or a virus. Preferably, the second intracellular pathogen is a virus.

The invention encompasses various types of assays, for example, in one embodiment, the first intracellular pathogen comprises a prokaryote (e.g., one or more of the preferred prokaryotes listed below), a eukaryote (e.g., one or more of the preferred eukaryotes listed below) and/or a virus (e.g., one or more of the preferred viruses listed below), and the second intracellular pathogen comprises a prokaryote (e.g., one or more of the preferred prokaryotes listed below).

In a further embodiment, the first intracellular pathogen comprises a prokaryote (e.g., one or more of the prokaryotes listed below), a eukaryote (e.g., one or more of the eukaryotes listed below) and/or a virus (e.g., one or more of the viruses listed below), and the second intracellular pathogen comprises a eukaryote (e.g., one or more of the preferred eukaryotes listed below).

In a further embodiment, the first intracellular pathogen comprises a prokaryote (e.g., one or more of the prokaryotes listed below), a eukaryote (e.g., one or more of the eukaryotes listed below) and/or a virus (e.g., one or more of the preferred viruses listed below, e.g., a parainfluenzavirus and/or e.g. an influenzavirus, a *rhinovirus*, a rotavirus, an enterovirus, a human immunodeficiency virus, a simian immunodeficiency virus, and/or a norovirus), and the second intracellular pathogen comprises a virus (e.g., one or more of the preferred viruses listed below, e.g., an influenza virus, and/or e.g. a *rhinovirus*, a rotavirus, an enterovirus, a human immunodeficiency virus or simian immunodeficiency virus, and/or a norovirus, and/or e.g. a parainfluenzavirus).

According to the invention, prokaryotes may include intracellular pathogens selected from *Bartonella, Bordetella, Brucella, Chlamydiales, Chlamidiaceae, Chlamydiae, Chlamydophila, Ehrlichia, Escherichia, Francisella, Legionella, Listeria, Mycobacterium, Mycobacterium, Rickettsiae, Salmonella, Shigella, Streptococcus, Yersinia.*

In particular, prokaryotes may include intracellular pathogens selected from *Bartonella grahamii, Bordetella pertussis, Brucella spp., Chlamydia trachomatis, Chlamydophila pneumoniae, Chlamydophila pecorum, Chlamydophila psittaci, Chlamydophila abortus, Chlamydophila felis, Chlamydophila caviae, Ehrlichia chaffeensis, Escherichia coli, Francisella tularensis, Legionella pneumophila, Listeria monocytogenes, Mycobacterium tuberculosis, Mycobacterium leprae, Rickettsiae, Salmonella enterica Serovar Typhimurium, Salmonella typhi, Shigella flexneri, Shigella dysenteriae, Streptococcus pyogenes, Yersinia pestis.*

According to the invention, eukaryotes may include intracellular pathogens selected from *Babesia, Cryptococcus, Cryptosporidium, Eimeria, Histoplasma, Leishmania, Plasmodium, Theileria, Toxoplasma, Trypanosoma.*

In particular, eukaryotes may include *Babesia spp., Cryptococcus neoformans, Cryptosporidium parvum, Eimeria spp., Histoplasma capsulatum, Leishmania mexicana, Leishmania donovani, Plasmodium berghei, Plasmodium yoelii, Theileria spp., Toxoplasma gondii, Trypanosoma cruzi.*

According to the Invention, Viruses may Include

Pneumovirinae, such as the *Pneumovirus* genus, including respiratory syncytial virus (RSV);

Morbilliviruses of the Paramyxoviridae family, such as the measles virus;

Enteroviruses of the Picornaviridae family, such as the Coxsackie viruses, echoviruses and enteroviruses;

mammalian Reoviridae, in particular orthoreoviruses (e.g. mammalian reoviruses) and/or rotaviruses;

Avian Reoviridae, in particular orthoreoviruses, such as avian reoviruses;

Metapneumoviruses of the Paramyxoviridae family, such as human metapneumovirus (HMPV);

Rubulaviruses of the Paramyxoviridae family, such as mumps virus;

Togaviridae such as Rubellavirus;

Coronaviridae, human coronaviruses, such as SARS coronavirus;

Rhinoviruses of the Picornaviridae family;

M-strains of *Rhinovirus;*

Varicella Zoster virus (VZV), also known as human herpes virus 2 (HHV3);

Polyomaviridae, such as the SV-40 *polyomavirus,* the BK *polyomavirus* JC *polyomavirus,* porcine circoviruses;

porcine picornaviruses;

swine vesicular disease virus (SVDV);

Teschen-Talfan virus;

Parvoviruses, such as canine parvovirus (CPV), or porcine parvoviruses, or Bocaviruses, e.g., human bocavirus;

Orthomyxoviridae, in particular influenza virus, e.g., influenza A virus, influenza B virus and influenza C virus.

Parainfluenza viruses (Ply), Paramyxoviridae paramyxovirinae, Parainfluenzavirus type 1, Parainfluenzavirus type 2, Parainfluenzavirus type 3, Parainfluenzavirus type 4, Parainfluenzavirus type 5;

Herpesviridae, herpes simplex virus 1 and 2;

Adenoviridae, such as the adenoviruses, including human and simian adenovirus, avian circoviruses;

an immunodeficiency virus such as human immunodeficiency virus (HIV) or simian immunodeficiency virus (SIV);

noroviruses; and/or

Birnaviridae, such as infectious bursal disease virus (also known as gumboro virus).

Thus, the first and/or second said first intracellular pathogen may comprise one or more intracellular pathogens selected from *Bartonella, Bordetella, Brucella, Chlamydia, Ehrlichia, Escherichia, Francisella, Legionella, Listeria, Mycobacterium, Mycobacterium, Rickettsiae, Salmonella, Shigella, Streptococcus, Yersinia, Babesia, Cryptococcus, Cryptosporidium, Eimeria, Histoplasma, Leishmania, Plasmodium, Theileria, Toxoplasma, Trypanosoma, Pneumovirinae,* the *Pneumovirus* genus, respiratory syncytial virus (RSV), Morbilliviruses of the Paramyxoviridae family, the measles virus, Enteroviruses of the Picornaviridae family, Coxsackie viruses, echoviruses and enteroviruses, mammalian Reoviridae, avian Reoviridae, orthoreoviruses, rotaviruses, Metapneumoviruses of the Paramyxoviridae family, human metapneumovirus (HMPV), Rubulaviruses of the Paramyxoviridae family, mumps virus, Togaviridae, Rubellavirus, Coronaviridae, human coronaviruses, SARS coronavirus, Rhinoviruses of the Picornaviridae family, M-strains of *Rhinovirus,* Varicella Zoster virus (VZV), human herpes virus 2 (HHV3), Polyomaviridae, SV-40 *polyomavirus*, the BK *polyomavirus* JC *polyomavirus*, porcine circoviruses, porcine picornaviruses, swine vesicular disease virus (SVDV), Teschen-Talfan virus, Parvoviruses, canine parvovirus (CPV), porcine parvoviruses, Orthomyxoviridae, in particular influenza virus, e.g., influenza A virus, influenza B virus and influenza C virus, Parainfluenza viruses (PIV), Paramyxoviridae paramyxovirinae, Parainfluenzavirus type 1, Parainfluenzavirus type 2, Parainfluenzavirus type 3, Parainfluenzavirus type 4, Parainfluenzavirus type 5, Herpesviridae, herpes simplex virus 1 and 2, Adenoviridae, adenoviruses, human and simian adenovirus, avian circoviruses, human immunodeficiency virus, simian immunodeficiency virus, norovirus, birnaviridae, infectious bursal disease virus (also known as gumboro virus).

For example, the second intracellular pathogen may preferably be, or comprise, a coronavirus, e.g., a SARS coronavirus, an enterovirus, a rotavirus, a *rhinovirus*, a human immunodeficiency virus, a simian immunodeficiency virus, or a norovirus. In further preferred embodiments, the second intracellular pathogen may be, for instance, an influenza virus, e.g., an influenza A virus or an influenza B virus.

The method is not limited to any particular type or strain of virus. For example, if the second intracellular pathogen is an influenza virus or a strain thereof, the virus may be influenza A virus, influenza B virus and influenza C virus. Preferred influenza A strains in the context of the invention include strains of subtypes H1N1 (e.g., human and/or swine H1N1), H1N2 (e.g., human and/or swine H1N2), H2N2, H2N3, H3N1, H3N2 (e.g., human and/or swine H3N2), H5N1, H7N2, H7N3, H7N7, H9N2, H10N7). Viruses in the methods of the invention may also be pandemic strains (i.e. strains to which the vaccine recipients and the general human population are immunologically naïve), such as H1 (e.g., H1N1), H2, H5, H7 or H9 subtype strains (in particular of influenza A virus). Thus, in the methods of the invention, an influenza A virus may have HA subtype H1, H2, H3, H4, H5, H6, H7, H8, H9, H10, H11, H12, H13, H14, H15 or H16. The invention may be used with an influenza A virus having NA subtype N1, N2, N3, N4, N5, N6, N7, N8 or N9.

The virus, e.g. an influenza A virus, may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. Typically, the virus may be a strain that is capable of human-to-human transmission, and so the strain's genome will usually include at least one RNA segment that originated in a mammalian (e.g. in a human or swine) influenza virus. It may include NS segment that originated in an avian, human or swine influenza virus.

The virus may be attenuated. The virus may be temperature-sensitive. The virus may be cold-adapted. The virus may be a reassortant strain, and may have been obtained by reverse genetics techniques [e.g. 1-5].

The methods of the invention may be used to test for the presence or absence of the first intracellular pathogen. That is, it may be unknown whether the first intracellular pathogen is present in the biological sample to be tested. The first intracellular pathogen may be present in the biological sample. The first intracellular pathogen may equally well not be present in the biological sample.

The second intracellular pathogen may or may not be present in the biological sample. Preferably, the second intracellular pathogen is known to be present in the biological sample. Alternatively, it may be unknown whether the second intracellular pathogen is present in the biological sample to be tested.

In preferred embodiments, the second intracellular pathogen is a virus, and it is unknown whether the first intracellular pathogen is present in the biological sample, i.e., the method of the invention is used to test for the presence or absence of the first intracellular pathogen in the presence of a virus.

The biological sample of the methods of the invention may also comprise, or be tested for, a third, fourth, fifth or further intracellular pathogen. Any such third or further intracellular pathogen may be as described above for the first or second intracellular pathogens. In preferred embodiments, it is unknown whether a third, fourth, fifth or further intracellular pathogen is present in the biological sample. In preferred embodiments, the methods of the invention are used to test for the presence or absence of a multitude of intracellular pathogens, e.g., for a third, fourth, fifth or further intracellular pathogen.

The Biological Sample

The invention can be used with various different biological samples. The sample may contain, e.g., as the first and/or second intracellular pathogen, a virus of interest. Such a sample may be tested for the possible presence of a first intracellular pathogen (e.g., a first virus) while the sample also contains a second intracellular pathogen (e.g., a second virus).

Typical samples to be tested with the invention include, but are not limited to:

- Laboratory samples.
- Clinical samples taken from patients e.g. from patients presenting symptoms of an infection, from whom respiratory swabs are taken to check for possible new pathogens, e.g., new viral strains. The pathogen may, e.g., be any of the viruses listed above, for example an enterovirus, a coronavirus, a herpesvirus or an influenza virus.
- Viral seeds, including master seed and working seeds. Such seed lots are used and tested during biologics production, where they form the basis of viral growth. The virus may be any of the viruses listed above, for example an enterovirus, a coronavirus, a herpesvirus or an influenza virus.

The presence of the second intracellular pathogen (e.g., a virus) may thus be desired, while the presence of the first intracellular pathogen is not desired. The method of the invention may be a test to confirm the absence of the first intracellular pathogen.

Likewise, the presence the second pathogen (e.g., virus) may be known, while the presence of the first intracellular pathogen is not desired and/or known.

Preferably, the sample is used solely for screening or testing purposes, rather than for testing within the process of manufacturing from said sample. The methods may advantageously be combined with other known testing methods.

The biological sample may also be, or may be derived from, an embryonated egg, e.g., an embryonated chicken egg, including the allantoic cavity, or a chick embryo.

The biological sample may also be, or be obtained or derived from, a cell or tissue culture, e.g. a growing cell or tissue culture, or a non-growing cell or tissue culture. Such a cultures may be a cell line of mammalian origin. Suitable cells of mammalian origin include, but are not limited to, hamster, cattle, primate (including humans and monkeys) and dog cells. Various cell types may be used, such as kidney cells, fibroblasts, retinal cells, liver cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc.

Preferably, said biological sample comprises or is derived from mammalian cells.

Preferred mammalian cell lines include: MDCK cells [6-9], derived from Madin Darby canine kidney; Vero cells [10-12], derived from African green monkey (*Cercopithecus aethiops*) kidney; or PER.C6 cells [13], derived from human embryonic retinoblasts. These cell lines are widely available e.g. from the American Type Cell Culture (ATCC) collection [14], from the Coriell Cell Repositories [15], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The original MDCK cell line is available from the ATCC as CCL-34, but derivatives of this cell line may also be used. For instance, reference 6 discloses a MDCK cell line that was adapted for growth in suspension culture ('MDCK 33016', deposited as DSM ACC 2219). Similarly, reference 16 discloses a MDCK-derived cell line that grows in suspension in serum-free culture ('B-702', deposited as FERM BP-7449). Reference 17 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 18 discloses MDCK cell lines with high susceptibility to infection, including 'MDCK.5F1' cells (ATCC CRL-12042). Any of these MDCK cell lines can be used.

The sample be also be, or be obtainable from, avian cell lines [e.g. refs. 19-21], including avian embryonic stem cells [19,22] and cell lines derived from ducks (e.g. duck retina), or from hens. Suitable avian embryonic stem cells, include the EBx cell line derived from chicken embryonic stem cells, EB45, EB14, and EB14-074 [23]. Chicken embryo fibroblasts (CEF), can also be used, etc.

The Population of Cells

In the method of the invention, a biological sample to be tested is contacted with a population of cells, in vivo or in vitro. The population of cells may be, or may be comprised in, an organism, including an embryo, e.g., a mammal, a rodent, mouse, rat, guinea pig, hamster, rabbit, chick, or non-human primate. The population of cells may also be cells in culture. Preferably, the population of cells is a cell culture (cultured cells). The population of cells may also be, for example, an embryonated egg, e.g., an embryonated chicken egg, including the allantoic cavity, or a chick embryo.

Generally, the population of cells may be as described above for the biological sample. Accordingly, the population of cells, or cultured cells, may be a cell line of mammalian origin. Preferably, said population of cells comprises or is derived from mammalian cells. In preferred embodiments of the invention, both the biological sample and the population of cells comprise, or are derived from, mammalian cells.

Suitable cells of mammalian origin are as described above for the biological sample. These include MDCK cells, Vero cells or PER.C6 cells. Any of the cell lines described above in connection with the biological sample, for example any of the MDCK cell lines described above, can be used as the population of cells.

Alternatives to mammalian cell lines as described above for the biological sample may also be used, e.g., the population of cells of the method of the invention may be an avian cell line.

In preferred embodiments, the population of cells express an oligonucleotide or polypeptide which is the inhibitory agent of the method of the invention. Said oligonucleotide may be an oligomeric compound as described in more detail herein below. Preferably, the cells in said population of cells are transfected and/or engineered to express the inhibitory agent. The expression of the inhibitory agent may be, from an expression vector. Vectors and methods for expression of sequences in cells, e.g, in mammalian cells are well known in the art. The inhibitory agent may be transiently expressed. More preferably, the inhibitory agent is stably expressed in the population of cells. That is, a nucleotide sequence, e.g., a DNA sequence, capable of expressing the inhibitory agent may be transiently transfected into the population of cells, i.e., the expression of the inhibitory agent in the population of cells may be by transient transfection of an expression vector. However, more preferably, a nucleotide sequence, e.g., a DNA sequence, capable of expressing the inhibitory agent is stably transfected into the population of cells, i.e., the expression of the inhibitory agent in the population of cells is by stable transfection, i.e., expression of the inhibitory agent is from a coding sequence stably integrated into the genome of the cells of said population of cells and/or stably propagated within the population of cells.

If the biological sample contains cells, then the biological sample may itself serve as the population of cells. In this case, step (i) of the processes of the invention will involve contacting the biological sample with an inhibitory agent, or the biological sample itself may express the inhibitory agent, as described above.

Incubation

The invention involves incubating cells (i.e., the population of cells and/or the biological sample of the process of the invention) under conditions that permit the reproduction of a first intracellular pathogen. Said conditions may also permit the survival, growth, reproduction and/or division of cells within the population of cells. The incubation may be in vivo or in vitro. Specific conditions for reproduction of the first intracellular pathogen and/or permitting cell survival, growth, reproduction and/or division of the population of cells will vary according to normal experiment design.

In preferred embodiments, said conditions may be conditions in which an organism serves as an incubator for the first intracellular pathogen.

When the population of cells of the invention is a cell culture, the incubating step of the method of the invention preferably involves incubating (i.e., culturing) the cell culture under conditions that permit cell survival, growth, reproduction and/or division. The cells will be capable, under normal conditions known to the person of ordinary skill in the area of the invention, of supporting reproduction of one or more of the intracellular pathogens described above (in the absence of an inhibitory agent specific to the intracellular pathogen that is to be allowed to reproduce). Thus, the step of further culturing the cells permits reproduction of pathogens in the culture. Pathogens that are thus allowed to reproduce, or the effects they produce in the culture (e.g. a phenotypic effect upon the population of cells), may then be observed. According to the methods of the invention, these first pathogens may be observed preferentially over a second pathogen, which is also present in the sample, but is inhibited from reproducing by the presence of a inhibitory agent that is specific for the second pathogen.

In general terms, conditions that permit reproduction of pathogens and/or the growth of suitable cells are well known in the art. Conditions permitting the survival, growth, reproduction and/or division of suitable cells are generally provided together with the cells when obtained from a commercial supplier.

Depending on the cell type and desired assays, cells may be grown in suspension, in adherent culture, or in microcarrier culture. Cells used with the invention may thus be adapted for growth in suspension. One suitable MDCK cell line that is adapted for growth in suspension culture is MDCK 33016 (deposited as DSM ACC 2219).

Rather than being grown in the presence of serum, cell lines may be grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for supporting replication of certain intracellular pathogens (i.e., the first intracellular pathogen of the methods of the invention). The cells growing in such cultures naturally contain proteins themselves.

In some embodiments, the population of cells may be incubated below 37° C. (e.g. 30-36° C.).

Observation, Testing

According to the invention, material arising from the incubation of the cells under conditions that permit cell growth is tested for first intracellular pathogen.

Generally, tests may be performed on cells themselves, on cell-containing culture fluid, or on cell-free culture fluid (e.g. on a supernatant of the culture). Such tests include both in vitro and in vivo tests. For example, one or more of the following tests may be performed:

Microscopy, including transmission electron microscopy.
Histological tests, e.g., cellular staining, e.g., histochemical, immunological or immunochemical staining.
Biochemical tests for retroviruses e.g. a RT assay.
Test for infectivity of a different cell-type e.g. to detect cytopathic effects.
Molecular genetic tests, such as PCR.
Animal inoculation tests e.g. into adult mice, suckling mice, guinea pigs, rabbits.
Infection of embryonated eggs.

The testing may be for a phenotypic effect, e.g., a cytopathic effect, e.g., a plaque in a cell culture, cell death, apoptosis. In some preferred embodiments, testing may be for inflammation or any phenotype or biological indicator, mediator or molecule associated with inflammation. Generally, any observable effect may be suitable.

A positive test result, e.g., the presence of a phenotypic or cytopathic effect, may be indicative of the presence in the biological sample of a first intracellular pathogen (i.e., an intracellular pathogen other than the second intracellular pathogen which cannot reproduce due to the presence of an inhibitory agent). The absence of an effect that may be attributed to a pathogen is indicative of the absence of the first intracellular pathogen, i.e., the absence of an intracellular pathogen that, under the conditions employed, would lead to an observable effect in the population of cells when said pathogen reproduces.

Usually, the invention will be accompanied by one or more control cultures. E.g. in one form of positive control, the sample and cells are cultured in the absence of the inhibitory agent and/or in the presence of a known pathogen. In examples of negative controls, the cells may be cultured in the absence of one or more pathogens, e.g., the second intracellular pathogen and/or the first intracellular pathogen, and/or in the absence of the biological sample, or both the sample and the inhibitory agent. Such controls permit ready comparisons to be made.

The Inhibitory Agent

According to the invention, in order to test for a first intracellular pathogen, cells are incubated in the presence of one or more agent inhibiting the survival and/or reproduction of a second intracellular pathogen. If said inhibitory agent(s) were not present, the second intracellular pathogen would reproduce in the cells, causing phenotypic effects, and the first and second intracellular pathogens may not be easily differentiated. The function of the inhibitory agent is to inhibit reproduction of the second intracellular pathogen under the culture conditions, thereby permitting the first intracellular pathogen to reproduce in preference to the second intracellular pathogen. Thus, according to the invention, intracellular pathogens may more easily be differentiated, and intracellular pathogens of interest (the first intracellular pathogen according to the claims or a further, e.g., a third intracellular pathogen) may more easily be observed.

Preferably, the inhibitory agent does not prevent survival, growth, reproduction and/or division of the population of cells. A slight negative impact on the cells may be tolerated, but, in the process of the invention, cell survival, growth, reproduction and/or division can still take place under the culture conditions in the presence of the inhibitory agent.

The inhibitory agent also does not prevent survival, multiplication and/or reproduction of pathogens for which the method is intended to test (e.g., the first intracellular pathogen according to the claims, or one or more further intracellular pathogens which herein may be referred to as third, fourth, fifth or further intracellular pathogens). Again, a slight negative impact may be tolerated, but the process is intended to permit reproduction and detection of the first intracellular pathogen if it is present in the sample. In the process of the invention, the inhibitory agent inhibits survival and/or reproduction of the second intracellular pathogen to a greater extent than the agent inhibits survival and/or reproduction of the first and/or further intracellular pathogen. That is, the inhibitory agent specifically, selectively or preferentially inhibits the second intracellular pathogen. Preferably, said inhibitory agent does not, or does not substantially, inhibit the survival, multiplication and/or reproduction first (and/or further) intracellular pathogen. Most preferably, the inhibitory agent inhibits survival and/or reproduction of the second intracellular pathogen completely.

When investigating different pathogens, it may thus be possible to use different inhibitory agents. An inhibitory agent may inhibit, or preferentially, a particular pathogen, but have no effect, or a much lesser effect, on a further pathogen, or on further pathogens. In this situation, the inhibitory agent is suitable for use with the invention where the presence of the first intracellular pathogen of the method of the invention is being tested, but because the agent inhibits the reproduction of a second intracellular pathogen, the agent would not be suitable when looking for said second pathogen.

In accordance with the preceding paragraphs, the invention also comprises embodiments wherein a second or further agent, inhibiting the reproduction of a third or further intracellular pathogen.

The inhibitory agent may be selected based on the type of intracellular pathogen that is to be inhibited. For example, if the second intracellular pathogen is a virus, e.g., an influenza virus, the inhibitory agent may be selected based on the type of virus, e.g., influenza A virus or influenza B virus. In such embodiment, some agents may act against both A and B viruses, whereas others are specific.

The inhibitory agent may be an antifungal agent. The inhibitory agent may also be an antiviral agent or an antibacterial agent. The inhibitory agent may be an antibiotic.

An inhibitory agent may be selected based on known characteristics of the life cycle of the second intracellular pathogen. The second intracellular pathogen may be lytic pathogen, i.e., it may cause the lysis of cells. When the second intracellular pathogen is lytic, the inhibitory agent preferably inhibits the life cycle of the second intracellular pathogen such that cell lysis is prevented. For example, in preferred embodiments, the inhibitory agent inhibits replication or gene expression in the second intracellular pathogen. Preferably the inhibitory agent targets one or more RNA species of the second intracellular pathogen such that reproduction and/or assembly of the second intracellular pathogen is prevented. For instance, when the second intracellular pathogen is an influenza virus, oseltamivir is less useful with the invention than other agents. Oseltamivir is active against influenza virus in vivo, but this activity is exerted extracellularly. As influenza virus is lytic, cell cultures will experience a large cytopathic effect before the antiviral compound can interfere with the viral life cycle under the conditions of the process. Generally, inhibitory agents that act extracellularly (including neuraminidase inhibitors for influenza virus) are not preferred. Preferably, the inhibitory agent inhibits or prevents the intracellular reproduction, growth, multiplication, replication, gene-expression, transcription, and/or translation of the second intracellular pathogen. For example, the inhibitory agent may inhibit gene-expression of the second intracellular pathogen. For example, the inhibitory agent may post-transcriptionally inhibit gene-expression of the second intracellular pathogen, for example by inhibition of mRNA translation, in particular by degradation of mRNA.

Preferred agents for use with the invention can at least partially inhibit or prevent reproduction, growth, multiplication, replication, gene-expression, transcription, and/or translation of an intracellular pathogen. More preferably, said inhibition or prevention is is at least substantially complete, most preferably complete.

Preferred agents for use with the invention can at least partially inhibit or prevent a phenotypic or cytopathic effect of the second intracellular pathogen, e.g., viral cytopathic effects, or can at least partially inhibit or prevent hemadsorption and/or hemagglutination. More preferably, agents for use with the invention inhibit or prevent viral cytopathic effects, hemadsorption and/or hemagglutination at least substantially completely, most preferably completely.

Suitable inhibitory agents include, but are not limited to, small organic compounds (e.g. molecular weight <1000 Da), oligomeric compounds, in particular interfering RNA molecules and antisense molecules. When the second intracellular pathogen is a virus, suitable inhibitory agents include small molecule antiviral drugs, and peptide inhibitors such as enfuvirtide.

Preferably, the agent comprises an oligomeric compound or moiety, e.g., a nucleic acid, an oligonucleotide, a nucleic acid derivative or an oligonucleotide derivative, including a modified nucleic acid or a modified oligonucleoside. The agent may inhibit the expression of a sequence (e.g., a gene) in the genome of the second intracellular pathogen, that is, the inhibitory agent may be directed against a target sequence.

Preferably the agent comprises an oligomeric compound or moiety that is capable of complementary base pairing with the target sequence. Preferably the agent is substantially complementary to a target sequence. The target sequence may be a nucleotide sequence present in, complementary to, encoded by and/or transcribed from the genome of the second intracellular pathogen. Preferably the oligomeric compound is capable of complementary base pairing with a nucleotide sequence transcribed from the genome of the second intracellular pathogen, e.g. with an mRNA, e.g. a mature mRNA. If the second intracellular pathogen is a virus, said transcribed sequence may also be within a complementary RNA or DNA (cRNA or cDNA) genome, i.e., a complementary genome sequence in relation to a plus-strand or minus-strand viral genome. Said transcribed sequence may also be a regulatory RNA molecule.

Preferably, the oligomeric compound is 80%, 82%, 84%, 86%, 88%, 90%, 92%, 94%, 96%, 98%, 99% or 100% complementary to the target sequence.

The agent comprising an oligomeric compound may be single-stranded or double-stranded. Likewise, the oligomeric compound may be single-stranded or a double-stranded. When the agent is a double-stranded oligomeric compound—i.e., a duplex—one of the two strands of said agent is capable of said complementary base-pairing with said nucleotide sequence present in, and/or transcribed from the genome of the second intracellular pathogen.

A portion or sequence of the agent that is capable of complementary base-pairing with a target sequence is referred to as being antisense to said sequence of said a target sequence. Thus, the agent may be an antisense oligomeric compound. An inhibitory agent that is an antisense oligomeric compound may act by any antisense-based mechanism of gene inhibition, e.g., an RNAse H, an RNAi (RNA interference) mechanism, a RISC-based mechanism. Herein, a RISC-based mechanism is a mechanism involving a RISC complex, including the RNAi mechanism. Agents that act by antisense-based mechanism of gene inhibition are well known in the art, and the person skilled in the art may adapt the structure of the agent accordingly. Preferably, the oligomeric compound acts by RNAi to inhibit the reproduction of the second intracellular agent. Thus, the inhibitory agent may be an interfering oligomeric compound, including an interfering RNA molecule, such as an siRNA (a short interfering RNA molecule).

A strand of an agent that is an oligomeric compound, e.g., an oligonucleotide, may be 19-80 monomers in length, preferably 19-75, 19-70, 19-65, 19-60, 19-55, 19-50, 19-45, 19-40, 19-35 or 19-30 monomers in length, preferably 19-29, 19-28, 19-27, or 19-26 monomers in length, e.g., 20-26, 21-26, 22-26, 23-26, 19-25, 20-25, 21-25, 22-25, 23-25, 19-24, 20-24, 21-24, 22-24, 23-24, 19-23, 20-23, 21-23, 22-23, 19-22, 20-22, 21-22, 19-21, 20-21 or 19-20 nucleotides in length. Said monomers are preferably capable of complementary base pairing with nucleic acids, and preferably comprise nucleic acid bases, nucleosides or nucleotides, e.g., ribonucleosides or deoxyribonucleotides or derivatives thereof. That is, said monomers are preferably capable of complementary base pairing to a target sequence in a manner that supports an antisense-based (e.g., RNAi) mechanism of inhibiting the expression of the target sequence. The agent may be a single strand capable of forming a hairpin structure, that is, by virtue of internal complementary base pairing, e.g., the agent may be a short hairpin RNA.

For example, agents that inhibit coronavirus, e.g., SARS coronavirus or influenza virus replication are known in the art. For instance, siRNA molecules targeting coronovirus are discussed and referenced in reference 24. Reference 25 discloses around 20 different siRNA molecules that target influenza A virus. Further siRNA work from the same group is disclosed in references 26 and 27. Influenza B virus was targeted in reference 28. Further interfering RNAs active against influenza virus are disclosed in references 29 and 30.

Preferably, regions of a virus targeted by oligomeric compounds are conserved among different subtypes and strains of the virus, e.g., between human, chicken, duck, horse, and/or swine influenza Influenza sequences are available from the influenza sequence database: www.flu.lanl.gov. Preferably, an oligomeric compound does not share identity with a known gene in the population of cells used in the methods of the invention, or does not interfere with the ability of the cells to permit the reproduction of said first intracellular pathogen. For example, oligomeric compounds targeting influenza virus may inhibit the expression of one or more of the HA, NA, M, NP, NS, PA, PB1, PB2, genes. The NP, PA, PB1 and/or PB2 genes are preferred for the selection of target sequences, in particular the NP and/or the PA genes are preferred targets.

Antisense nucleic acids active against influenza virus replication are also known in the art. For instance, reference 31 discloses antiviral morpholino antisense oligonucleotides.

Whereas inhibitory agents used in vivo must have acceptable toxicity, pharmacokinetic profiles, half lives, etc., these considerations are not so important with processes of the invention. For instance, there are many potent antiviral (e.g., anti-influenza) compounds that have been rejected for routine use in humans because of unfavourable systemic pharmaceutical properties, but which may be used with the invention. Similarly, issues of delivery that are relevant to siRNA or antisense molecules are less important when dealing with cell cultures. References 25 already reports that its siRNA molecules are active against influenza virus growing in MDCK culture, and reference 28 also focused on cultured cells. Even so, delivery systems can still be used for in vitro work. For instance, delivery of siRNA to cultured cells to inhibit influenza virus replication was reported in reference 32 using virosomes. Reference 33 further reports the use of polycation-based systems to facilitate their delivery into cells. Reference 34 used plasmid constructs to anti-influenza siRNAs in MDCK cultures. Lentiviral vectors were used with cultured MDCK cells in reference 35.

Preferably, the inhibitory agent is expressed in the population of cells of the methods of the invention, e.g., in a cultured cell line or a genetically engineered organism, as described above in connection with the population of cells. Thus, the inhibitory agent may comprise a single-stranded and/or double-stranded oligonucleotide that is expressed in the population of cells. As described above, preferably a nucleotide sequence expressing the inhibitory agent is stably propagated in said population of cells, and the inhibitory agent is stably expressed in said cell population. In preferred embodiments, the inhibitory agent is expressed as an oligonucleotide as described above, e.g., as a single-stranded compound capable of forming a hairpin structure (e.g., a short hairpin RNA), as two separate strands capable of forming an siRNA duplex, as a single-stranded interfering agent, as an antisense agent, as a compound capable of complementary base pairing with a nucleotide sequence transcribed from the genome of the second intracellular pathogen, as a compound capable of inhibiting reproduction of an intracellular pathogen by an antisense, e.g., an RNAi mechanism, etc. Preferably, the inhibitory agent is a hairpin RNA. Thus, the population of cells preferably contains a nucleotide sequence encoding and expressing the inhibitory agent of the methods of the invention. The inhibitory agent is preferably a hairpin RNA and/or comprises an antisense RNA.

For example, siRNA expression vectors have been described in reference 34.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The term "one or more" encompasses "one", "more than one", 2, 3, 4, 5, 6, 7, 8, 9, 10, 11, 12, 13, 14, 15, 16, 17, 18, 19, 20, 21, 22, 23, 24, 25, 26, . . . etc.

The term "two or more" encompasses "two", "more than two", 3, 4, 5, 6, 7, 8, 9, 10, 11, 12, 13, 14, 15, 16, 17, 18, 19, 20, 21, 22, 23, 24, 25, 26, . . . etc.

Unless specifically stated, a process comprising a step of mixing two or more components does not require any specific order of mixing. Thus components can be mixed in any order. Where there are three components then two components can be combined with each other, and then the combination may be combined with the third component, etc.

BRIEF DESCRIPTION OF DRAWINGS

There are no drawings.

MODES FOR CARRYING OUT THE INVENTION

Example

In one preferred embodiment of the method of the invention, a biological sample derived from a MDCK cell culture contains influenza virus. The sample is contacted with a uninfected (pathogen-free) population of MDCK cells (a test culture) in a plaque assay. Reproduction of the influenza virus in the test culture is inhibited by RNAi, which allows plaque formation in the test culture to be observed and attributed to a pathogen other than the influenza virus.

The test culture may be a monolayer of MDCK cells in 1% semisolid agar. An appropriate amount of siRNA directed against a suitable influenza virus target sequence, e.g., the influenza virus nucleoprotein (NP) or acidic polymerase (PA gene, is introduced into the cells of the test culture (e.g., 2.5 nmol per $1\times10^7$ MDCK cells) by methods known in the art. The siRNA sequences may be, for example, as disclosed in references 25 and 27, i.e., sense oligonucleotide 5'-GGAUCUUAUUUCUUCGGAGdTdT-3' (SEQ ID NO: 1) and antisense oligonucleotide 5'-dTdTC-CUAGAAUAAAGAAGCCUC-3' (SEQ ID NO: 2) directed against the nucleoprotein (NP) gene; or sense oligonucleotide 5'-GCAAUUGAGGAGUGCCUGAdTdT-3' (SEQ ID NO: 3), and antisense oligonucleotide 5'-dTdTCGUUAA-CUCCUCACGGACU-3' (SEQ ID NO: 4) directed against the acidic polymerase gene. After 7-10 hours, appropriate amounts of the sample (e.g., 2-fold or 10-fold serial dilutions) are added to test cultures. The titer or content of influenza virus in the test culture and/or the inhibition of influenza inhibition by the siRNA may be monitored, for example, by subjecting serial dilutions of test culture supernatant to a haemaglutation (HA) assay, or by RNA extraction, reverse transcription and PCR employing methods that are well known in the art. After a suitable incubation time, e.g. two days, the test culture is assessed for plaque formation by staining with crystal violet. If the influenza virus does not reproduce during incubation, any plaques visualized by the staining are attributable to a pathogen other than the influenza virus.

In addition to the controls mentioned above, siRNA specific for GFP may also be introduced into GFP-expressing MDCK cells followed by virus infection (e.g., with influenza virus) or addition of the tested sample. GFP expression may be assayed by flow cytometry.

Materials and Methods

MDCK cells are grown by methods well known in the art, e.g., in DMEM containing 10% heat-inactivated FCS, 2 mM 1-glutamine, 100 units/ml penicillin, and 100 μg/ml streptomycin at 37° C. under a 5% CO2/95% air atmosphere.

Influenza virus stocks are grown in the allantoic cavity of 10-day-old embryonated chicken eggs (Charles River Laboratories, Wilmington, Mass.) at 37° C. Allantoic fluid is harvested 48 h after virus inoculation and stored at −80° C. Virus titer is measured by hemagglutination or plaque assays.

RNA oligonucleotides for siRNAs are commercially available or may be chemically synthesized according to methods known in the art. In order to obtain a duplex siRNA, equimolar amounts of complementary oligonucleotides are mixed, heated to 95° C. for 5 min, then annealed by reducing the temperature, e.g., by 1° C. every 30 sec until 35° C., then by 1° C. every min until 5° C. siRNA duplexes are analyzed for completion of duplex formation by gel electrophoresis.

The suitability and efficacy of siRNAs inhibiting the reproduction of the second pathogen, e.g., influenza virus, may be assessed separately in MDCK cells. Logarithmic-phase MDCK cells may be trypsinized, washed, and resuspended in serum-free medium, e.g., RPMI medium 1640, at $2\times10^7$ cells per ml. Cells (0.5 ml) are mixed with siRNA and electroporated at 400 V and 975 μF by using a Gene Pulser apparatus (Bio-Rad). Electroporated cells are divided and cultured in DMEM for 8 h. The culture medium is then removed and a suitable amount of virus in DMEM, 0.3% BSA (Sigma), 10 mM Hepes, 100 units/ml penicillin, and 100 μg/ml streptomycin, is added to each well. After incubation for 1 h at room temperature, 2 ml of DMEM buffer containing 0.3% BSA (Sigma), 10 mM Hepes, 100 units/ml penicillin, 100 μg/ml streptomycin, and 4 μg/ml trypsin is added to each well. Cells are then cultured at 37° C. under 5% CO and the virus titer monitored in the supernatant.

The hemagglutination assay is carried out in V-bottom 96-well plates. Serial dilutions (e.g., 2-fold) of samples are mixed with an equal volume of a 0.5% suspension (vol/vol) of erythrocytes, e.g., chicken erythrocytes available from Charles River Laboratories). After incubation on ice for one hour, wells are assessed for adherent, homogeneous layers of erythrocytes, which indicate hemagglutination.

For plaque assays, serial dilutions of samples are added onto monolayers of MDCK cells in 1% semisolid agar. After two days, plaques are visualized by staining with crystal violet.

It will be understood that the invention has been described by way of example only and modifications may be made whilst remaining within the scope and spirit of the invention.

REFERENCES

[1] Hoffmann et al. (2002) *Vaccine* 20:3165-3170.
[2] Subbarao et al. (2003) *Virology* 305:192-200.
[3] Liu et al. (2003) *Virology* 314:580-590.
[4] Ozaki et al. (2004) *J. Virol.* 78:1851-1857.
[5] Webby et al. (2004) *Lancet* 363:1099-1103.
[6] WO97/37000.
[7] Brands et al. (1999) *Dev Biol Stand* 98:93-100.
[8] Halperin et al. (2002) *Vaccine* 20:1240-7.
[9] Tree et al. (2001) *Vaccine* 19:3444-50.
[10] Kistner et al. (1998) *Vaccine* 16:960-8.
[11] Kistner et al. (1999) *Dev Biol Stand* 98:101-110.
[12] Bruhl et al. (2000) *Vaccine* 19:1149-58.
[13] Pau et al. (2001) *Vaccine* 19:2716-21.
[14] http://www.atcc.org/
[15] http://locus.umdnj.edu/
[16] EP-A-1260581 (WO01/64846).
[17] WO2006/071563.
[18] WO2005/113758.
[19] WO03/076601.
[20] WO2005/042728.
[21] WO03/043415.
[22] WO01/85938
[23] WO2006/108846
[24] Wu and Chan (2006) *Expert Opin Investig Drugs.* 15(2):89-97.
[25] Ge et al. (2003) *PNAS USA* 100:2718-23.
[26] Ge et al. (2004) *Virus Res.* 102(1):37-42.
[27] Thompkins et al (2004) *PNAS USA* 101:8682-86
[28] Gao et al. (2006) *Antivir Ther.* 2006; 11(4):431-8.
[29] US-2006/0275265.
[30] US-2004/0242518.
[31] US-2007/000466.
[32] Huckriede et al. (2007) *J Liposome Res.* 17(1):39-47.
[33] Thomas et al. (2005) *Exp Opin Biol Ther* 5:495-505.
[34] Li et al. (2005) *Avian Dis.* 49(4):562-73.
[35] Hui et al. (2004) *J Gen Virol.* 85:1877-84.

The invention claimed is:

1. A process for testing in production of a biologic for the presence of a first viral pathogen in a biological sample obtained from a cell culture, the process comprising the steps of:
   (i) providing a sample obtained from the cell culture for production of the biologic from a second virus;
   (ii) contacting the sample with an inhibitory agent, wherein said agent is an oligomeric compound that binds through complementary base pairing to a nucleotide sequence present in, encoded by and/or transcribed from the genome of the second virus, and the second virus is known to be present in the sample;
   (iii) incubating the sample obtained from the cell culture under conditions that permit the reproduction of said first viral pathogen; and
   (iv) testing material arising from step (iii) for said first viral pathogen by microscopy, a reverse transcription-based biochemical test for retroviruses, detection of a cytopathic effect, a PCR-based molecular genetic test, an animal inoculation test, infection of embryonated eggs, or any combination thereof.

2. The process of claim 1, wherein said first viral pathogen comprises one or more viral pathogens selected from Pneumovirinae, the *Pneumovirus* genus, respiratory syncytial virus (RSV), Morbilliviruses of the Paramyxoviridae family, the measles virus, Enteroviruses of the Picornaviridae family, Coxsackie viruses, echoviruses and enteroviruses, mammalian Reoviridae, avian Reoviridae, orthoreoviruses, rotaviruses, Metapneumoviruses of the Paramyxoviridae family, human metapneumovirus (HMPV), Rubulaviruses of the Paramyxoviridae family, mumps virus, Togaviridae, Rubellavirus, Coronaviridae, human coronaviruses, SARS coronavirus, Rhinoviruses of the Picornaviridae family, M-strains of *Rhinovirus*, Varicella Zoster virus (VZV), human herpes virus 2 (HHV3), Polyomaviridae, SV-40 *polyomavirus*, the BK *polyomavirus* JC *polyomavirus*, porcine circoviruses, porcine picornaviruses, swine vesicular disease virus (SVDV), Teschen-Talfan virus, Parvoviruses, canine parvovirus (CPV), porcine parvoviruses, Bocaviruses, Orthomyxoviridae, influenza A virus, influenza B virus and influenza C virus, Parainfluenza viruses (PIV), Paramyxoviridae paramyxovirinae, Parainfluenzavirus type 1, Parainfluenzavirus type 2, Parainfluenzavirus type 3, Parainfluenzavirus type 4, Parainfluenzavirus type 5, Herpesviridae, herpes simplex virus 1 and 2, Adenoviridae, adenoviruses, human and simian adenovirus, avian circoviruses, birnaviridae, infectious bursal disease virus.

3. The process of claim 1, wherein said second virus comprises a viral pathogen selected from Pneumovirinae, the *Pneumovirus* genus, respiratory syncytial virus (RSV), Morbilliviruses of the Paramyxoviridae family, the measles virus, Enteroviruses of the Picornaviridae family, Coxsackie viruses, echoviruses and enteroviruses, mammalian Reoviridae, avian Reoviridae, orthoreoviruses, rotaviruses, Metapneumoviruses of the Paramyxoviridae family, human metapneumovirus (HMPV), Rubulaviruses of the Paramyxoviridae family, mumps virus, Togaviridae, Rubellavirus, Coronaviridae, human coronaviruses, SARS coronavirus, Rhinoviruses of the Picornaviridae family, M-strains of *Rhinovirus*, Varicella Zoster virus (VZV), human herpes virus 2 (HHV3), Polyomaviridae, SV-40 *polyomavirus*, the BK *polyomavirus* JC *polyomavirus*, porcine circoviruses, porcine picornaviruses, swine vesicular disease virus (SVDV), Teschen-Talfan virus, Parvoviruses, canine parvovirus (CPV), porcine parvoviruses, Bocaviruses, Orthomyxoviridae, influenza A virus, influenza B virus and influenza C virus, Parainfluenza viruses (PIV), Paramyxoviridae paramyxovirinae, Parainfluenzavirus type 1, Parainfluenzavirus type 2, Parainfluenzavirus type 3, Parainfluenzavirus type 4, Parainfluenzavirus type 5, Herpesviridae, herpes simplex virus 1 and 2, Adenoviridae, adenoviruses, human and simian adenovirus, avian circoviruses, birnaviridae, infectious bursal disease virus.

4. The process of claim 1, wherein it is unknown whether the first viral pathogen is present in the biological sample to be tested.

5. The process of claim 1, wherein one or both of said biological sample and said population of cells comprise or are derived from mammalian cells or avian cells.

6. The process of claim 5, wherein said mammalian cells comprise one or more of hamster, cattle, primate, human, monkey and dog cells.

7. The process of claim 5, wherein said mammalian cells comprise one or more of kidney cells, fibroblasts, retinal cells, liver cells, lung cells.

8. The process of claim 5, wherein said mammalian cells are MDCK cells, Vero cells, or PER C6 cells.

9. The process of claim 1, wherein said oligomeric compound acts by RNAi to inhibit the reproduction of the second virus.

10. The process of claim 9, wherein the agent comprising said oligomeric compound is double-stranded.

11. The process of claim 1 wherein a test result of step (iv) is obtained within 12 months.

12. A process of for testing in production of a biologic for the presence of a first viral pathogen in a biological sample obtained from a cell culture, the process comprising the steps of:

(i) providing a sample obtained from the cell culture for production of the biologic from a second virus;

(ii) contacting the sample with an inhibitory agent, wherein said agent is an oligomeric compound that binds through complementary base pairing to a nucleotide sequence present in, encoded by and/or transcribed from the genome of the second virus, and the second virus is known to be present in the sample;

(iii) incubating the sample obtained from the cell culture under conditions that permit the reproduction of said first viral pathogen; and (iv) testing material arising from step (iii) for said first viral pathogen by microscopy, a reverse transcription-based biochemical test for retroviruses, detection of a cytopathic effect, a PCR-based molecular genetic test, an animal inoculation test, infection of embryonated eggs, or any combination thereof, wherein the second virus is influenza A virus and the cell culture is for preparation of an influenza vaccine.

13. The process of claim 1, wherein after the step (i), the sample is contacted with a population of cells not infected with the second virus.

14. A process for testing for the presence of a first viral pathogen in a biological sample, the process comprising the steps of:

(i) contacting the biological sample with a population of cells in the presence of an inhibitory agent, wherein said agent is an oligomeric compound that binds through complementary base pairing to a nucleotide sequence present in, encoded by and/or transcribed from the genome of the second virus, and the second virus is known to be present in the sample;

(ii) incubating the cells under conditions that permit the reproduction of said first viral pathogen while the second virus is inhibited from reproducing by the presence of the inhibitory agent; and (iii) testing material arising from step (ii) for said first viral pathogen by microscopy, a reverse transcription-based biochemical test for retroviruses, detection of a cytopathic effect, a PCR-based molecular genetic test, an animal inoculation test, infection of embryonated eggs, or any combination thereof.

15. The process of claim 14, wherein said first viral pathogen comprises one or more viral pathogens selected from Pneumovirinae, the *Pneumovirus* genus, respiratory syncytial virus (RSV), Morbilliviruses of the Paramyxoviridae family, the measles virus, Enteroviruses of the Picornaviridae family, Coxsackie viruses, echoviruses and enteroviruses, mammalian Reoviridae, avian Reoviridae, orthoreoviruses, rotaviruses, Metapneumoviruses of the Paramyxoviridae family, human metapneumovirus (HMPV), Rubulaviruses of the Paramyxoviridae family, mumps virus, Togaviridae, Rubellavirus, Coronaviridae, human coronaviruses, SARS coronavirus, Rhinoviruses of the Picornaviridae family, M-strains of *Rhinovirus*, Varicella Zoster virus (VZV), human herpes virus 2 (HHV3), Polyomaviridae, SV-40 *polyomavirus*, the BK *polyomavirus* JC *polyomavirus*, porcine circoviruses, porcine picornaviruses, swine vesicular disease virus (SVDV), Teschen-Talfan virus, Parvoviruses, canine parvovirus (CPV), porcine parvoviruses, Bocaviruses, Orthomyxoviridae, influenza A virus, influenza B virus and influenza C virus, Parainfluenza viruses (PIV), Paramyxoviridae paramyxovirinae, Parainfluenzavirus type 1, Parainfluenzavirus type 2, Parainfluenzavirus type 3, Parainfluenzavirus type 4, Parainfluenzavirus type 5, Herpesviridae, herpes simplex virus 1 and 2, Adenoviridae, adenoviruses, human and simian adenovirus, avian circoviruses, birnaviridae, infectious bursal disease virus.

16. The process of claim 14, wherein said second virus comprises a viral pathogen selected from Pneumovirinae, the *Pneumovirus* genus, respiratory syncytial virus (RSV), Morbilliviruses of the Paramyxoviridae family, the measles virus, Enteroviruses of the Picornaviridae family, Coxsackie viruses, echoviruses and enteroviruses, mammalian Reoviridae, avian Reoviridae, orthoreoviruses, rotaviruses, Metapneumoviruses of the Paramyxoviridae family, human metapneumovirus (HMPV), Rubulaviruses of the Paramyxoviridae family, mumps virus, Togaviridae, Rubellavirus, Coronaviridae, human coronaviruses, SARS coronavirus, Rhinoviruses of the Picornaviridae family, M-strains of *Rhinovirus*, Varicella Zoster virus (VZV), human herpes virus 2 (HHV3), Polyomaviridae, SV-40 *polyomavirus*, the BK *polyomavirus* JC *polyomavirus*, porcine circoviruses, porcine picornaviruses, swine vesicular disease virus (SVDV), Teschen-Talfan virus, Parvoviruses, canine parvovirus (CPV), porcine parvoviruses, Bocaviruses, Orthomyxoviridae, influenza A virus, influenza B virus and influenza C virus, Parainfluenza viruses (PIV), Paramyxoviridae paramyxovirinae, Parainfluenzavirus type 1, Parainfluenzavirus type 2, Parainfluenzavirus type 3, Parainfluenzavirus type 4, Parainfluenzavirus type 5, Herpesviridae, herpes simplex virus 1 and 2, Adenoviridae, adenoviruses, human and simian adenovirus, avian circoviruses, birnaviridae, infectious bursal disease virus.

17. The process of claim 14, wherein it is unknown whether the first viral pathogen is present in the biological sample to be tested.

18. The process of claim 14, wherein one or both of said biological sample and said population of cells comprise or are derived from mammalian cells or avian cells.

19. The process of claim 18, wherein said mammalian cells comprise one or more of hamster, cattle, primate, human, monkey and dog cells.

20. The process of claim 5, wherein said mammalian cells comprise one or more of kidney cells, fibroblasts, retinal cells, liver cells, lung cells.

21. The process of claim 5, wherein said mammalian cells are MDCK cells, Vero cells, or PER C6 cells.

22. The process of claim 14, wherein said oligomeric compound acts by RNAi to inhibit the reproduction of the second virus.

23. The process of claim 22, wherein the agent comprising said oligomeric compound is double-stranded.

24. The process of claim 14 wherein a test result of step (iv) is obtained within 12 months.

25. The process of claim 14, wherein the second viral pathogen is influenza A virus and the cell culture is for preparation of an influenza vaccine.

26. The process of claim 14, wherein after the step (i), the sample is contacted with a population of cells not infected with the second virus.

\* \* \* \* \*

SEQUENCE LISTING

<160> NUMBER OF SEQ ID NOS: 4

<210> SEQ ID NO 1

```
<211> LENGTH: 21
<212> TYPE: DNA
<213> ORGANISM: Artificial Sequence
<220> FEATURE:
<223> OTHER INFORMATION: Sense siRNA oligonucleotide
<220> FEATURE:
<221> NAME/KEY: misc_feature
<223> OTHER INFORMATION: /note="Combined DNA / RNA"

<400> SEQUENCE: 1
ggaucuuauu ucuucggagt t                                              21

<210> SEQ ID NO 2
<211> LENGTH: 21
<212> TYPE: DNA
<213> ORGANISM: Artificial Sequence
<220> FEATURE:
<223> OTHER INFORMATION: Antisense siRNA oligonucleotide
<220> FEATURE:
<221> NAME/KEY: misc_feature
<223> OTHER INFORMATION: /note="Combined DNA / RNA"

<400> SEQUENCE: 2
ttccuagaau aaagaagccu c                                              21

<210> SEQ ID NO 3
<211> LENGTH: 21
<212> TYPE: DNA
<213> ORGANISM: Artificial Sequence
<220> FEATURE:
<223> OTHER INFORMATION: Sense siRNA oligocucleotide
<220> FEATURE:
<221> NAME/KEY: misc_feature
<223> OTHER INFORMATION: /note="Combined DNA / RNA"

<400> SEQUENCE: 3
gcaauugagg agugccugat t                                              21

<210> SEQ ID NO 4
<211> LENGTH: 21
<212> TYPE: DNA
<213> ORGANISM: Artificial Sequence
<220> FEATURE:
<223> OTHER INFORMATION: Antisense siRNA oligonucleotide
<220> FEATURE:
<221> NAME/KEY: misc_feature
<223> OTHER INFORMATION: /note="Combined DNA / RNA"

<400> SEQUENCE: 4
ttcguuaacu ccucacggac u                                              21
```